United States Patent
Muraki et al.

[11] Patent Number: 6,042,267
[45] Date of Patent: Mar. 28, 2000

[54] X-RAY IMAGE PICKUP APPARATUS FOR INTRAORAL RADIOGRAPHY

[75] Inventors: Tetsuhiko Muraki; Hitoshi Asai; Kazuhisa Miyaguchi, all of Hamamatsu; Akifumi Tachibana, Kyoto; Masakazu Suzuki, Kyoto; Susumu Kirimura, Kyoto, all of Japan

[73] Assignees: Hamamatsu Photonics K.K., Hamamatsu; J. Morita Manufacturing Corporation, Kyoto, both of Japan

[21] Appl. No.: 09/056,935

[22] Filed: Apr. 8, 1998

[30] Foreign Application Priority Data

Apr. 9, 1997 [JP] Japan ................................. 9-091101

[51] Int. Cl.$^7$ ........................................... A61B 6/14
[52] U.S. Cl. ........................... 378/169; 378/168; 378/191
[58] Field of Search .................... 378/169, 168, 378/191, 98.3, 98.8; 250/368

[56] References Cited

U.S. PATENT DOCUMENTS

| | | | |
|---|---|---|---|
| 4,303,572 | 12/1981 | Hatanaka et al. | 260/37 SB |
| 5,228,430 | 7/1993 | Sakamoto | 128/6 |
| 5,331,166 | 7/1994 | Yamamoto et al. | |
| 5,550,380 | 8/1996 | Sugawara et al. | 250/370.11 |

FOREIGN PATENT DOCUMENTS

| | | |
|---|---|---|
| 87 11 389 | 12/1987 | Germany. |
| 42 35 527 | 4/1993 | Germany. |
| 44 02 114 | 7/1995 | Germany. |
| 44 46 960 | 4/1996 | Germany. |
| 2-10973 | 1/1990 | Japan. |
| 5-130990 | 5/1993 | Japan. |
| 7-280944 | 10/1995 | Japan. |

Primary Examiner—David V. Bruce
Assistant Examiner—Michael J. Schwartz
Attorney, Agent, or Firm—Pillsbury Madison & Sutro LLP

[57] ABSTRACT

A phosphor, an optical fiber plate containing lead particles, a CCD, and an X-ray shielding member consisting of copper tungsten are sequentially stacked on a substrate from an X-ray incident surface side and sealed in a container made of a light-shielding synthetic resin. The substrate has projecting portions projecting toward the direction of X-ray incident along three sides of the X-ray incident surface. Each of these projecting portions has an overhang portion projecting toward the optical fiber plate. The overhang portions are close to or in contact with corresponding side surfaces of the optical fiber plate so that the optical fiber plate is fixed at a predetermined position. The container has, in the inner surface, convex portions corresponding to the projecting portions, so the substrate is fixed in the container. The output signal from the CCD is sent to an external display unit via a cable extracted from the convex portion of the container through an FPC connector and an FPC provided on a surface opposite to the incident surface.

6 Claims, 8 Drawing Sheets

X-RAY IMAGE PICKUP APPARATUS FOR INTRAORAL RADIOGRAPHY

BACKGROUND OF THE INVENTION

1. Field of the Invention

The present invention relates to an X-ray image pickup apparatus and, more particularly, to a compact X-ray image pickup apparatus which is inserted into an oral cavity and used for intraoral radiograph taking a X-ray image of a dentition.

2. Related Background Art

In dental treatment, an intraoral X-ray imaging system using a solid-state image sensing device such as a CCD (Charge Coupled Device) is widely used to obtain an X-ray photographic image of the oral cavity, and particularly, a dentition. This X-ray photographic image is called an intraoral radiograph.

A conventional intraoral X-ray imaging system is disclosed in, e.g., Japanese Patent Laid-Open No. 7-280944. FIG. 5 is a view showing the entire arrangement of this system. FIGS. 6A to 6C are sectional views showing some X-ray image pickup apparatuses used in this system.

As shown in FIG. 5, an X-ray source 20 for irradiating a beam of X-rays and an X-ray image pickup apparatus 22 for intraoral radiograph are opposed each other while sandwiching a dentition 21 of a patient as a subject. The X-ray image pickup apparatus 22 is connected to a control unit 24 for controlling the entire system, through a cable 23 for transmitting image signals and supplying driving power. The control unit 24 is also connected to a monitor 25 for displaying the X-ray photographic image and a printer 26 for printing the displayed image.

The internal structure of the X-ray image pickup apparatus 22 will be described next with reference to FIGS. 6A to 6C. FIG. 6A is a cross-sectional view of the X-ray image pickup apparatus viewed from the direction of X-ray beam incident surface. FIG. 6B is a longitudinal sectional view including the cable portion. FIG. 6A corresponds to a section taken along a line A—A in FIG. 6B, and FIG. 6B corresponds to a section taken along a line B—B in FIG. 6A. FIG. 6C is a sectional view taken along the line B—B of the apparatus shown in FIG. 6A when the cable 23 is extracted from a surface opposite to the X-ray beam incident surface.

In the X-ray image pickup apparatus 22, a phosphor 1 for emitting visible light in response to x-ray incidence, an optical fiber plate 2 for transmitting the resulting visible light image, a CCD 3 for converting the transmitted visible light image into an electrical signal, a substrate 5 supporting the CCD 3 et al., and an X-ray shielding member 4 using lead or the like to absorb the X-ray and prevent it from passing through the surface opposite to the X-ray incident surface are stacked and sealed in a container 14 consisting of a synthetic resin having insulating and light-shielding properties. The cable 23 for extracting the output electrical signal from the CCD 3 and supplying driving power is electrically connected to the CCD 3 and extracted outward from the side surface or lower surface of the container 14, as shown in FIG. 6B or 6C.

The operation of this conventional apparatus will be described next with reference to FIGS. 5 and 6A to 6C. As shown in FIG. 5, X-rays emitted from the X-ray source 20 are partially interrupted by the dentition 21 and the silhouette image of this are projected on the incident surface of X-ray image pickup apparatus 22. In the X-ray image pickup apparatus 22 shown in FIGS. 6A to 6C, the incident X-rays are transmitted through the container 14 and absorbed by the phosphor 1. The phosphor emits the visible light corresponding to the intensity of incident X-rays. That is, a visible light image corresponding to the X-ray silhouette image is obtained. This visible light image is guided to the CCD 3 through the optical fiber plate 2. The CCD 3 has two-dimensionally arrayed pixels, so incident light is converted into an electrical signal in units of pixels. Of the X-ray components which have not been absorbed, X-ray components which have passed through the container 14, the phosphor 1, the optical fiber plate 2, the CCD 3, and the substrate 5 reach the X-ray shielding member 4 so most components are absorbed. For this reason, the amount of X-ray emerging from the lower surface of the container 14 is suppressed, so the exposed dose of the patient is minimized. Degradation in image caused when X-ray components which have been transmitted through the lower surface of the apparatus and reflected by another member are incident again from the lower surface can also be prevented.

The output electrical signal from the CCD 3 is sent to the control unit 24 through the cable 23 and processed image corresponding to the X-ray silhouette image of the dentition (intraoral radiograph) is displayed on the monitor 25, as shown in FIG. 5. In addition, a desired image can be printed out using the printer 26.

Japanese Patent Laid-Open No. 2-10973 discloses a technique of directly forming a phosphor on a solid-state image sensing device without using any optical fiber plate. With this technique, an X-ray incident on an apparatus 22 is transmitted through an incident window 31 and absorbed by a phosphor 1. Since the fluorescent light can be directly converted into an electrical signal by a CCD 3, no optical fiber plate is required, and the apparatus can be made compact. An X-ray shielding member 4 consisting of a polyimide resin and having a thickness of 1 mm is formed on the X-ray incident surface side excluding the incident window 31.

SUMMARY OF THE INVENTION

Such an X-ray image pickup apparatus using in the oral cavity must be made as compact as possible such that the patient does not suffer a pain in use. For this reason, in the apparatus shown in FIGS. 6A to 6C, particularly, the optical fiber plate 2 must be made small. On the other hand, to use effectively the image sensing area of the CCD 3, the optical fiber plate 2 must completely cover the image sensing area of the CCD 3. However, as the optical fiber plate 2 and CCD 3 become compact, the positions of these elements become difficult to adjust. From the viewpoint of manufacturing cost, limitations are imposed in making the size of the optical fiber plate 2 close to that of the image sensing area of the CCD 3. Since the optical fiber plate 2 is manufactured large in consideration of a positional shift in setting, limitations are imposed on size reduction of the entire apparatus.

On the other hand, in the apparatus shown in FIGS. 7A and 7B, although the optical fiber plate 2 is omitted, the X-ray transmitted through the phosphor 1 is directly incident on the CCD 3 to generate noise. Additionally, to absorb effectively the X-ray with the X-ray shielding member 4 made of a polyimide resin, the X-ray shielding member 4 must be much thicker than a member of lead or the like. This increases the thickness of the entire apparatus, so no low profile can be obtained.

The present invention has been made in consideration of the above problems, and has as its object to provide a compact X-ray image pickup apparatus for intraoral radiography, which minimizes the exposed dose on a patient.

In order to achieve the above object, the present invention is image pickup apparatus comprising (1) a phosphor which emits a visible light in response to an incident X-ray, (2) an optical fiber plate formed into a plate shape by bundling a plurality of optical fibers and having the X-ray phosphor on an X-ray incident surface formed by end faces of fibers, (3) a solid-state image sensing device constituted by two-dimensionally pixels array which converts the visible light image into an electrical signal and having the optical fiber plate on a light incident surface, (4) an X-ray shielding member arranged on a back plate of the solid-state image sensing device to absorb and shield the X-ray, (5) a substrate for disposing the solid-state image sensing device via the X-ray shielding member, having an electrode extraction terminal electrically connected to a driving power supply terminal of the solid-state image sensing device and an output terminal of the electrical signal, and, on X-ray incident surface, a plurality of projecting portions projecting to a direction of an X-ray incident around the optical fiber plate from at least three sides so that the side surfaces of the projecting portions are in contact with or close to corresponding side surfaces of the optical fiber plate, (6) a container for sealing the substrate together with components stacked on the substrate, and (7) a flexible cable having one end electrically connected to the electrode extraction terminal and the other end extracted outside the container and connected to an external driving power supply and an image display unit.

With this arrangement, the X-ray coming into the container is converted into visible light by the phosphor, sent to the solid-state image sensing device through the optical fiber plate, converted into an electrical signal, and extracted. By sending the electrical signal to an external display unit through a cable, an image corresponding to the X-ray image is displayed. The substrate for fixing the optical fiber plate and the like has projecting portions, and these projecting portions are formed at positions so as to sandwich the side surfaces of optical fiber plate from at least three directions. With the projecting portions, the optical fiber plate can be properly positioned. For this reason, the optical fiber plate can have almost the same size as that of the image sensing area of the solid-state image sensing device, so the optical fiber plate can be made compact. A variation in image can also be prevented. Since the X-ray shielding member is arranged on the lower surface of the solid-state image sensing device, the X-ray transmitted through the solid-state image sensing device is absorbed by the X-ray shielding member. The X-ray does not pass through the surface of the container opposite to the X-ray incident surface, so the excess X-ray exposed dose on the patient can be reduced.

Preferably, each of the projecting portions of the substrate has an overhang portion toward a corresponding side surface of the optical fiber plate so that a distal end of the overhang portion is in contact with or close to the side surface of the optical fiber plate. With this arrangement, since only the overhang portions need be accurately manufactured, fabrication is facilitated. In addition, the X-ray shielding member can cover a larger area.

Preferably, the container has a projecting portion at a position corresponding to each of the projecting portions on an inner surface on an X-ray incident surface side. With this arrangement, the substrate can be properly fixed in the container.

Preferably, the X-ray shielding member is formed from a thin flat copper tungsten member. Copper tungsten has a good affinity to a ceramic and high capability for shielding the X-ray.

The container may have a projecting portion for accommodating an output electrode terminal electrically connected to the electrode extraction terminal on a surface opposite to an X-ray incident surface so that one end of the cable may be connected to the output electrode terminal in the projecting portion. With this arrangement, the lower surface of the container projects only at the cable extraction portion, and the remaining portion can have a low profile.

The optical fiber of the optical fiber plate may be formed by mixing of lead or lead oxide particles into molten glass. With this arrangement, the X-ray transmitted through the phosphor and reaching the optical fiber plate is partially absorbed by lead.

The apparatus may further comprise a thin FPC (Flexible Printed Circuit) connector electrically connected to the electrode extraction terminal, and an FPC detachably connected to the FPC connector, and the cable may be connected to the FPC. With this arrangement, the cable and the X-ray image detecting apparatus main body are connected through the FPC connected to the thin FPC connector. The FPC and FPC connector is detachable and can be easily exchanged.

The present invention will be more fully understood from the detailed description given hereinbelow and the accompanying drawings, which are given by way of illustration only and are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will be apparent to those skilled in the art from this detailed description.

DESCRIPTION OF THE PREFERRED EMBODIMENTS

Figure 1A:
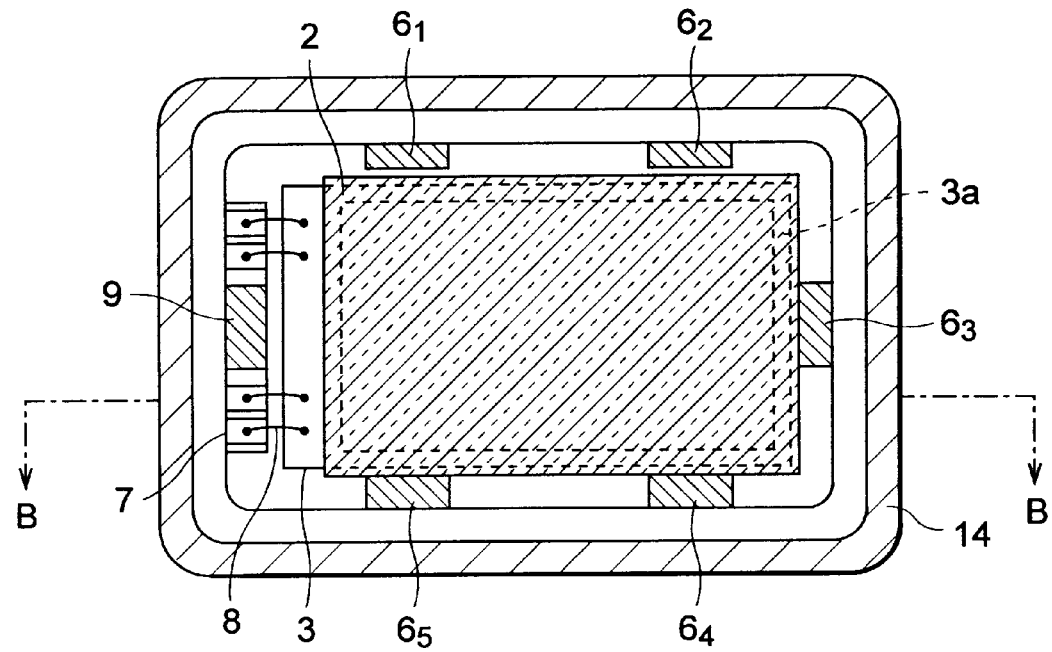
FIGS. 1A and 1B are cross-sectional and longitudinal sectional views, respectively, showing an embodiment of the present invention.

Embodiments of the present invention will be described below with reference to the attached drawings. The same reference numerals denote the same constituent elements throughout the drawings, and a duplicated description will be omitted. Some parts in the drawings have exaggerated dimensions or shapes for the descriptive convenience: the dimensions or shapes do not always agree with the actual dimensions or shapes.

Figure 1B:
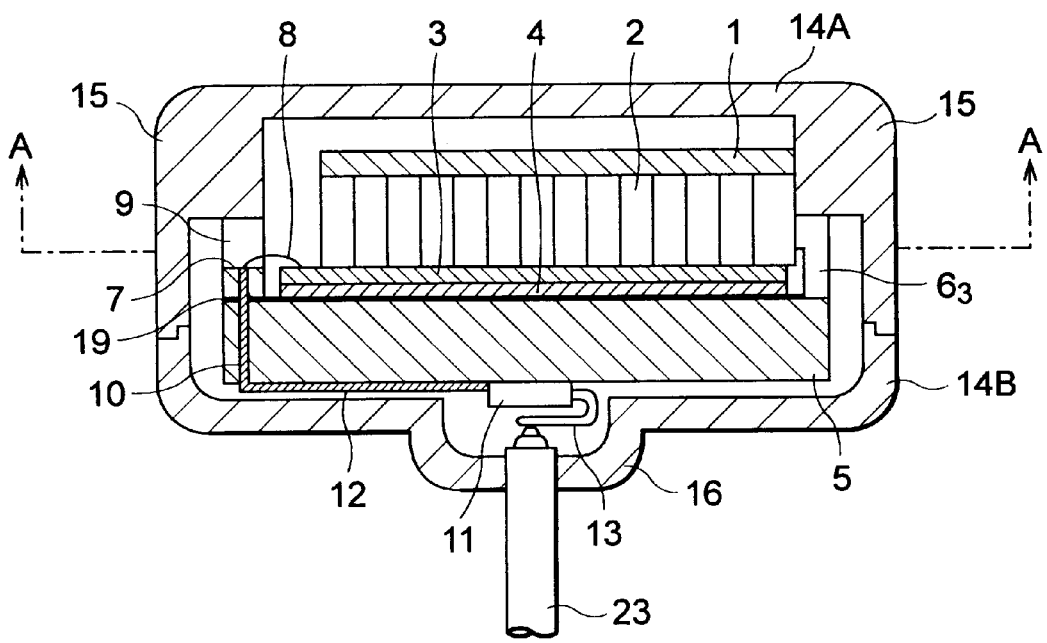
Figure 2:
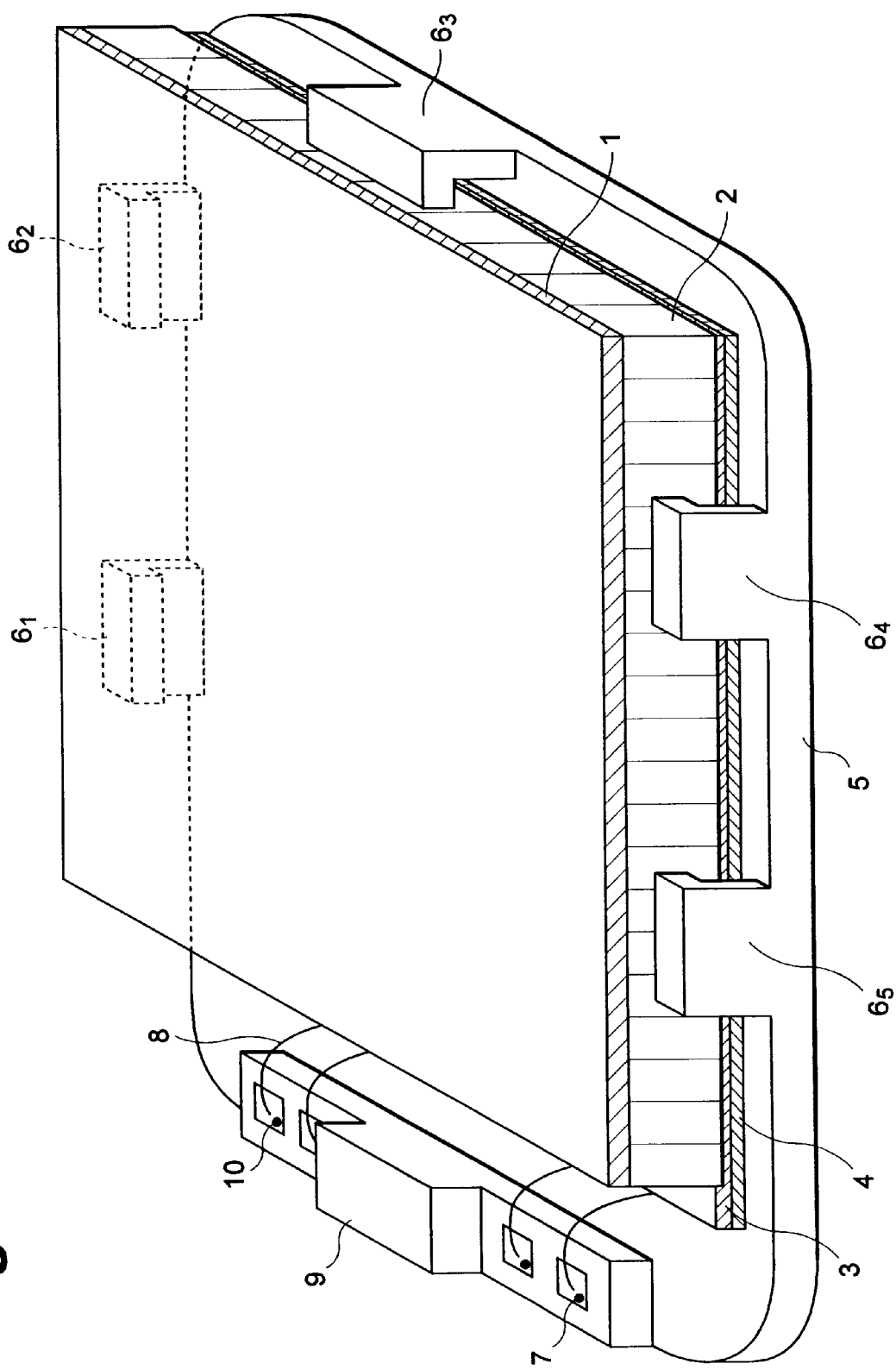
FIG. 2 is a perspective view of internal components of the embodiment shown in FIGS. 1A and 1B.

FIGS. 1A and 1B are sectional views showing the arrangement of an embodiment of the present invention. FIG. 1A is a cross-sectional view when viewed from the X-ray incident surface side, and FIG. 1B is a longitudinal sectional view when viewed from a side surface side. FIG. 2 is a perspective view showing the internal structure, i.e., the structures of components.

As shown in FIGS. 1A, 1B, and 2, a bundle of optical fibers containing lead particles for absorbing an X-ray is arranged such that the optical axes of optical fibers are perpendicular to the incident surface, thereby forming a flat optical fiber plate 2. A phosphor 1 for generating fluorescent light upon receiving an X-ray is applied or deposited on the X-ray incident surface side of the optical fiber plate 2.

The optical fiber plate 2 is disposed on the light incident surface side of a CCD 3 in which pixels for performing photoelectric conversion are two-dimensionally arrayed to generate an electrical signal corresponding to an input image. The optical fiber plate 2 completely covers an effective screen area 3a where the pixels of the CCD 3 are arrayed. The CCD 3 is fixed on a ceramic substrate 5 via a thin flat X-ray shielding member 4 consisting of copper tungsten.

A plurality of projecting portions $6_1$ to $6_5$ projecting toward the X-ray incident surface are formed on the X-ray incident surface side of the substrate 5 along three sides of the surface. On each of two opposing sides two projecting portions $6_1$ and $6_2$ ($6_4$ and $6_5$) are formed respectively, and on the remaining side one projecting portion $6_3$ is formed. Only the uppermost portion of each projecting portion $6_1$ to $6_5$ projects inward, i.e., toward the optical fiber plate 2. The overhang portion of a projecting portion $6_3$ formed on one side of the substrate 5 other than the two opposing sides contacts a corresponding side surface of the optical fiber plate 2. The overhang portions of projecting portions $6_1$ and $6_2$ or projecting portions $6_4$ and $6_5$ on one of the two opposing sides contact a corresponding side surface of the optical fiber plate 2, and the remaining overhang portions are arranged close to a corresponding side surface of the optical fiber plate 2. The distance between the projecting portions $6_1$ to $6_5$ and the optical fiber plate 2 is preferably 0.3 mm or less to properly adjust the fixing position of the optical fiber plate 2.

Electrode extraction terminals 7 are arranged on one side of the substrate 5 on the X-ray incident surface side, where no projecting portions $6_1$ to $6_5$ are formed, to be spaced apart from the optical fiber plate 2. The electrode extraction terminals 7 are wire-bonded to the electrodes of the CCD 3 through wires 8. A projecting portion 9 whose upper surface is almost flush with that of each projecting portion $6_1$ to $6_5$ is formed on the electrode extraction terminal 7 portion at a position opposite to the projecting portion $6_3$. The electrode extraction terminals 7 have, at the respective terminal positions, via holes extending through the substrate 5 from the X-ray incident surface to the other surface. An FPC connector 11 is arranged at the substantially central portion of a surface of the substrate 5 opposite to the X-ray incident surface. Each electrode extraction terminal 7 and the FPC connector 11 are electrically connected through an interconnection 12 formed through the via hole 10. As the interconnection 12, an interconnection consisting of tungsten or molybdenum manganese and plated with nickel or gold is preferably used.

The substrate 5 on which the above members are mounted is sealed in a container 14 formed from a resin such as ABS resin having insulating and light-shielding properties. Convex portions 15 are formed on the incident-side inner surface of the container 14 at positions corresponding to the projecting portions 6 and 9. These convex portions 15 are pressed against the projecting portions 6 and 9 to fix the substrate 5 in the container 14. As a result, all components are fixed in the container 14. A convex portion 16 is formed on a surface of the container 14 opposite to the X-ray incident surface to cover the FPC connector 11. An FPC 13 is detachably connected to the FPC connector 11 in the convex portion 16. The FPC 13 is soldered to a cable 23. The cable 23 is extracted outside from the convex portion 16. With this arrangement, the thickness of the entire container can be reduced except the cable extraction portion. Since the FPC 13 and the FPC connector 11 can be freely detached, the FPC 13 and the cable 23 can be easily exchanged.

The assembling steps of this embodiment will be described next with reference to FIGS. 3A to 3G. In all figures the non-necessary parts due to explanation are not indicated.

Figure 3A:
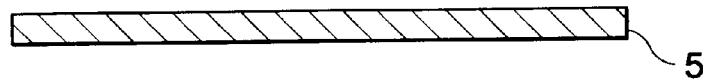
FIGS. 3A to 3G are explanatory views showing the steps in assembling the embodiment shown in FIGS. 1A and 1B.
Figure 3B:
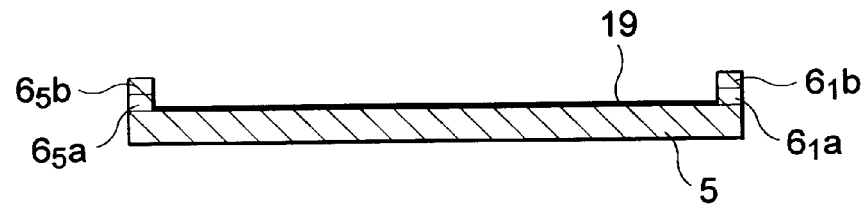
Figure 3C:
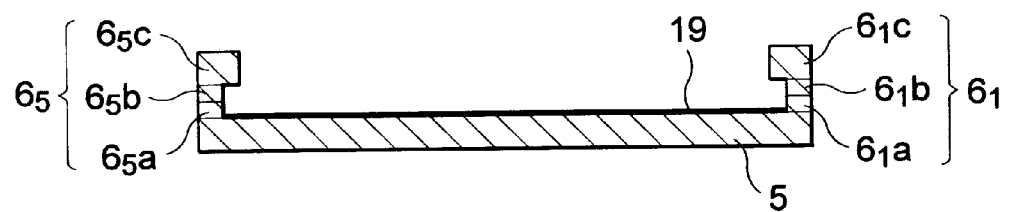

First, a plurality of ceramic plates $6_n$a to $6_n$c (n is an integer from 1 to 5) are stacked on the substrate 5 constituted by a flat ceramic plate as shown in FIG. 3A, as shown in FIGS. 3B and 3C, to form the projecting portions $6_1$ to $6_5$. At this time, in the respective projecting portions, e.g., the projecting portions $6_1$ and $6_5$ only the uppermost portions $6_1$c and $6_5$c have a large width, respectively. Since only the uppermost portions contact the optical fiber plate 2, the lower portions $6_1$a, $6_5$a, $6_1$b, and $6_5$b need not be properly positioned, as shown in FIG. 3B. Proper positioning is required only when the uppermost portions $6_1$c and $6_5$c are to be formed, as shown in FIG. 3C. The electrode extraction terminals 7, the projecting portion 9, the via holes 10, and the like shown in FIG. 2 are simultaneously formed, although they are not illustrated.

Figure 3D:
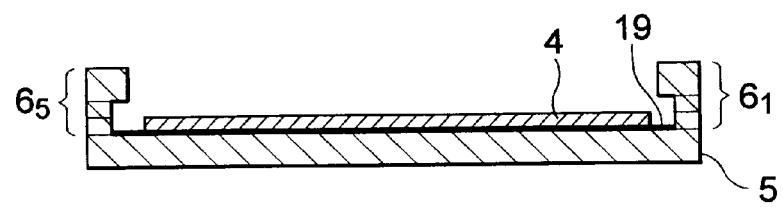

After formation of the projecting portions 6, to $6_5$, a thin flat X-ray shielding member 4 consisting of copper tungsten is brazed at the central portion of the X-ray incident surface of the substrate 5, as shown in FIG. 3D. The X-ray shielding member 4 may be fixed before or during formation of the projecting portions $6_1$ to $6_5$.

As the X-ray shielding member, lead can be effectively used. However, since lead is relatively soft, a flat film can hardly be formed at a high accuracy. To the contrary, copper tungsten can be used to form a flat film at a high accuracy. In addition, copper tungsten which is widely used as a heat dissipation member for a ceramic package has high versatility and good affinity to a ceramic. A conventional X-ray shielding member made of lead has a thickness of 0.25 mm. The present inventor has confirmed from experiments that the copper tungsten plate must have a thickness of 0.49 mm to realize the same X-ray shielding effect as that of the conventional member.

Figure 3E:
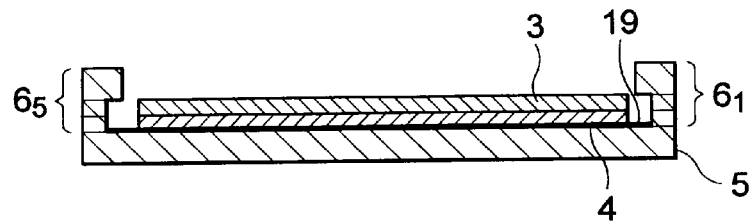

After this, as shown in FIG. 3E, the CCD 3 is bonded to the X-ray shielding member 4 using a conductive resin, so the potential of the X-ray shielding member 4 and the substrate potential of the CCD 3 are held at the same level. At this time point, the electrodes of the CCD 3 and the electrode extraction terminals 7 are preferably connected through the wires 8 to obtain electrical interconnections, as shown in FIG. 2.

Figure 3F:
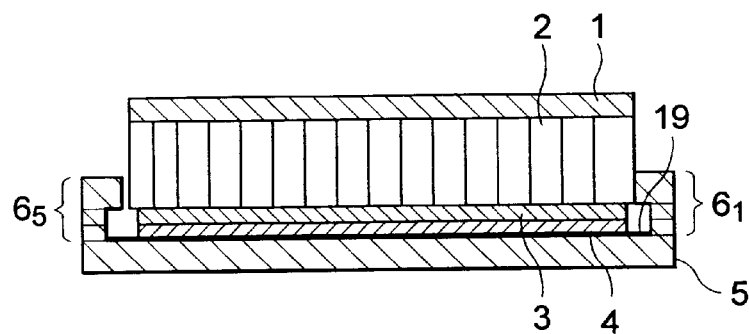

Subsequently, as shown in FIG. 3F, the optical fiber plate 2 is fixed on the CCD 3 with an adhesive resin. The phosphor 1 is deposited or applied on the X-ray incident surface side of the optical fiber plate 2 in advance. As shown in FIG. 3F, only the uppermost ceramic layers of the projecting portions 6 project toward the optical fiber plate 2. When the optical fiber plate 2 is mounted on the CCD 3 while two of three sides having the projecting portions 6 are made lower than the remaining two sides, i.e., the entire substrate 5 is slightly tilted, the optical fiber plate 2 always abuts against the overhang portions of the projecting portions 6 on the lower sides. For this reason, the fixing position of the optical fiber plate 2 can be accurately adjusted.

To effectively use the pixels of the CCD 3 to obtain a high-resolution image, the optical fiber plate 2 must cover the pixel portion as the image pickup portion of the CCD 3. According to this embodiment, since the positions of the optical fiber plate 2 and the CCD 3 can be accurately adjusted, the sectional area of the optical fiber plate 2 can be made as small as that of the pixel portion of the CCD 3. Therefore, the entire apparatus can be made compact.

Figure 3G:
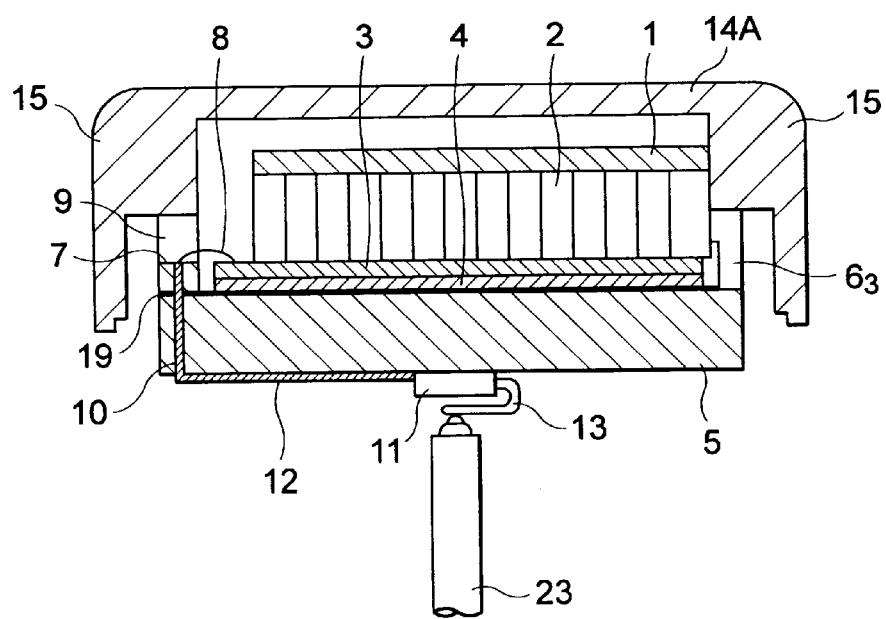

The substrate 5 on which the X-ray pickup device which has been manufactured in the above manner is fixed is fitted in a container 14A on the incident surface side, as shown in FIG. 3G. At this time, the substrate 5 can be properly fitted in the container 14A by making the convex portions 15 on the inner surface of the container 14A correspond to the projecting portions 6 and 9 of the substrate 5. The FPC 13 soldered to the cable 23 is detachably connected to the FPC connector 11 formed on the lower surface of the substrate 5.

When the container 14A and a container 14B, which sandwich the substrate 5, are bonded, the substrate 5 and the X-ray pickup device can be fixed in the container 14. The convex portion 16 is formed on a surface of the container 14B opposite to the X-ray incident surface side such that the FPC connector 11 is covered with the convex portion 16. With this arrangement, the thickness of the entire container can be reduced except the cable extraction portion. In addition, since the FPC 13 and the FPC connector 11 are detachable, the FPC 13 and the cable 23 can be easily exchanged.

Figure 5:
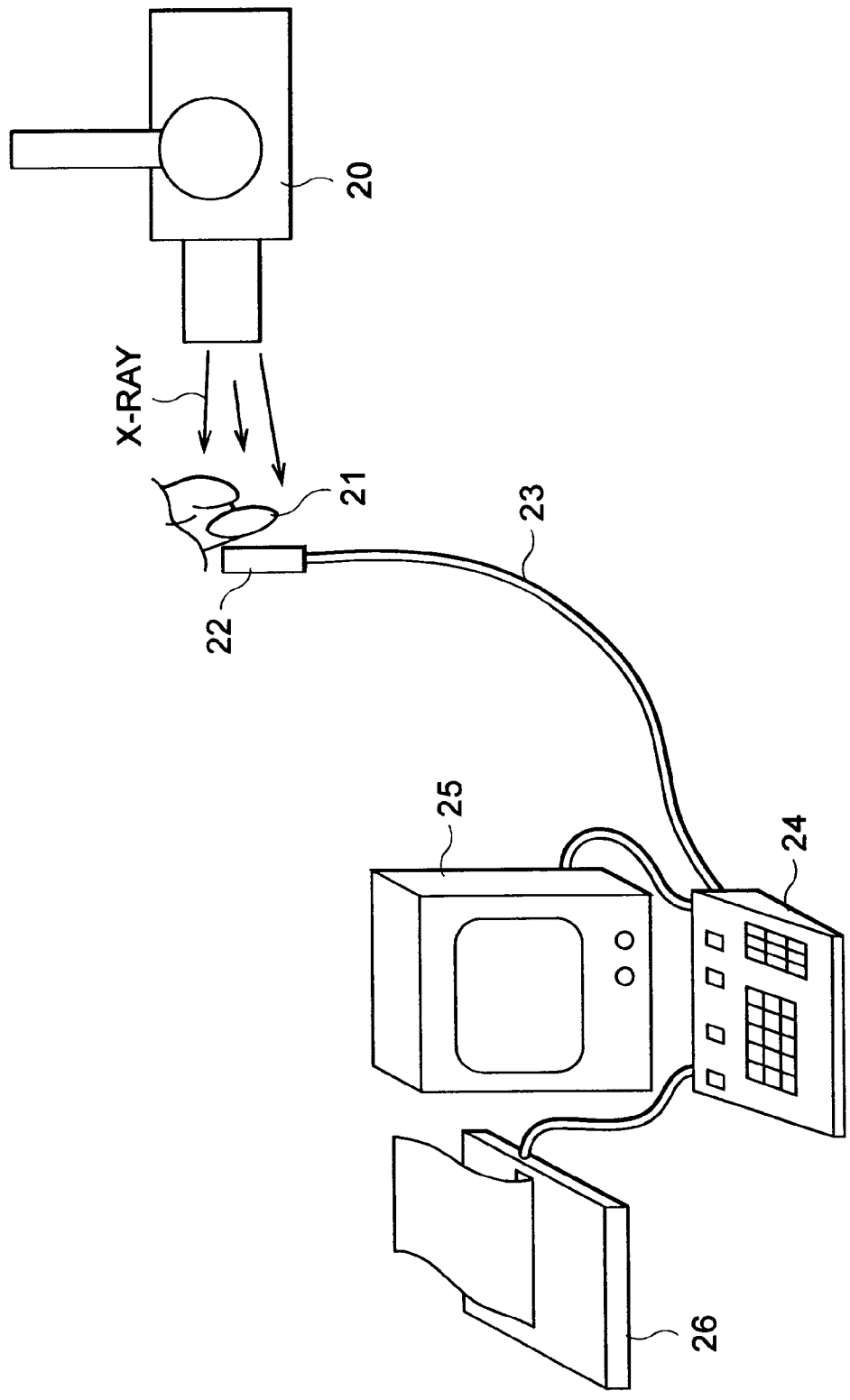
FIG. 5 is a view showing the arrangement of a general intraoral X-ray imaging system.
Figure 6A:
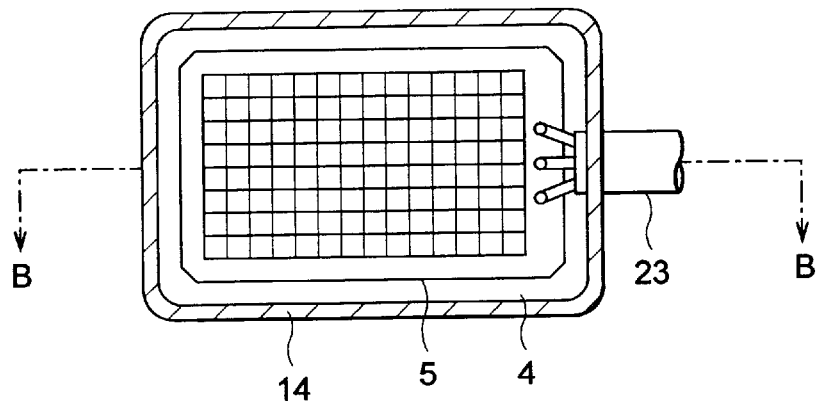
FIGS. 6A to 6C are sectional views showing a conventional X-ray image pickup apparatus used in the system shown in FIG. 5.
Figure 6B:
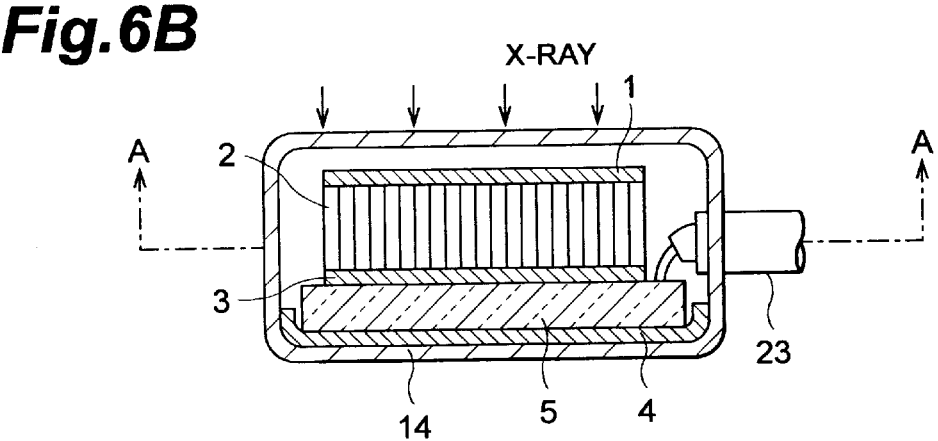
Figure 6C:
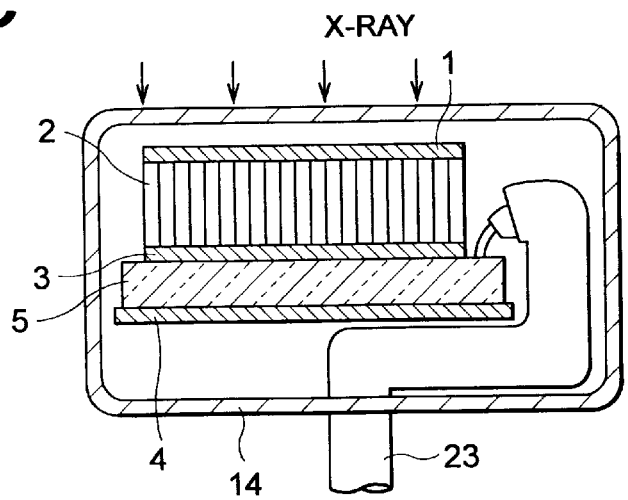
Figure 7A:
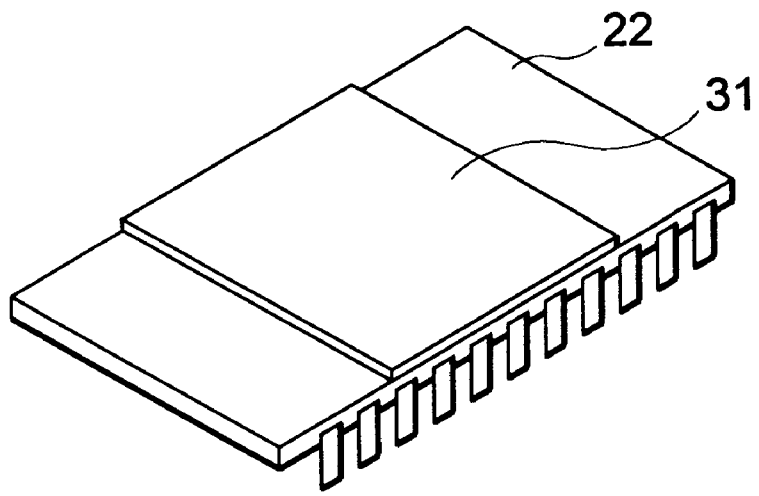
FIGS. 7A and 7B are perspective and sectional views, respectively, showing another conventional X-ray image pickup apparatus used in the system shown in FIG. 5.
Figure 7B:
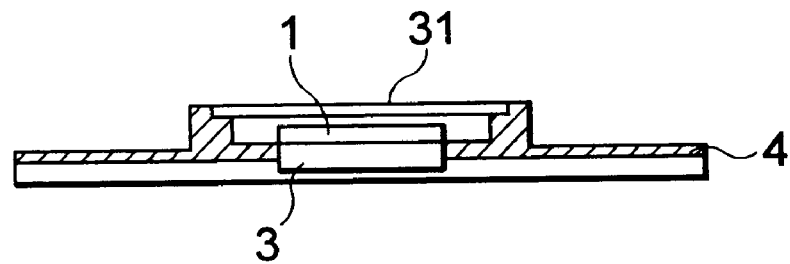

The operation of this apparatus applied to the X-ray imaging system shown in FIG. 5 will be described next. The arrangement of the X-ray imaging system is the same as that of the prior art except this apparatus. More specifically, an X-ray emitted from an X-ray source 20 projects a silhouette image of a patient's dentition 21, i.e. an intraoral radiograph, the incident surface of an apparatus 22.

The internal operation of the apparatus 22 will be described with reference to FIG. 1. Upon receiving the X-ray, the phosphor 1 emits a visible light image corresponding to the incident X-ray image, i.e. the intraoral radiograph, from a surface opposite to the incident surface. This visible light image is transmitted to the CCD 3 by the optical fiber plate 2. Most X-ray components transmitted which are not absorbed by the phosphor 1 are absorbed by lead in the optical fiber plate 2 and rarely reach the CCD 3, so the CCD 3 can detect a clear image without noise due to the X-ray. If lead is not contained in the optical fiber plate 2, the optical fiber plate 2 must have a sufficient thickness to absorb the X-ray image to suppress noise due to the X-ray. However, in this embodiment, the X-ray absorbance of the optical fiber plate 2 is improved to lower the X-ray transmittance. For this reason, the transmitted or scattered X-ray can be absorbed by the thin optical fiber plate 2, and the amount of X-ray reaching the CCD 3 can be reduced, so both the high sensitivity and thin profile can be simultaneously realized.

The CCD 3 converts the visible light image transmitted through the optical fiber plate 2 into an electrical signal corresponding to the image by two-dimensionally pixels array. Driving power for the CCD 3 is supplied from an external driving power supply through the cable 23, the FPC 13, the FPC connector 11, the interconnection 12, the electrode extract ion terminal 7, and the wire 8 (FIGS. 1A and 1B). The image electrical signal is sent from the CCD 3 to an external control unit 24 shown in FIG. 5 through another wire 8, the electrode extraction terminal 7, the interconnection 12, the FPC connector 11, the FPC 13, and the cable 23, and processed in the control unit 24, so the transmitted visible light image corresponding to the intraoral radiograph (X-ray silhouette image of the dentition 21) is displayed on the monitor.

The X-ray transmitted through the CCD 3 is absorbed by the x-ray shielding member 4. Therefore, the amount of X-ray transmitted through a surface of the X-ray image pickup apparatus 22 opposite to the incident surface can be decreased, so the X-ray exposed dose on the patient can be suppressed. In addition, since X-ray incidence from the surface opposite to the incident surface on the CCD 3 due to scattering or the like can be suppressed, noise can be reduced.

In this embodiment, by using the projecting portions 6 for position adjustment in fixing the optical fiber plate 2, the accuracy of position adjustment can be increased. In addition, in fixing the optical fiber plate 2 on the CCD 3, when the substrate 5 is tilted such that the side of the projecting portion $6_3$ to contact the optical fiber plate 2 becomes low, position adjustment of the optical fiber plate 2 is further facilitated.

Preferably, the projecting portions 6 do not continuously formed. If the projecting portions are integrated to have a frame shape, an excess adhesive spreads on the frame in stacking the optical fiber plate 2, resulting in a disadvantage in accommodating the substrate 5 in the container 14.

In addition, in this embodiment, the cable 23 is extracted from the convex portion 16 formed at the central portion on the lower surface opposite to the incident surface. The entire apparatus 22 has a low profile except this convex portion 16. For this reason, when the apparatus is inserted into the oral cavity in any directions, the cable 23 does not contact the upper or lower jaw. In addition, the relatively thick cable extraction portion of the convex portion 16 does not reach the deep in the oral cavity even in radiographying posterior teeth, so the patient does not suffer a pain in use of the apparatus.

Figure 4A:
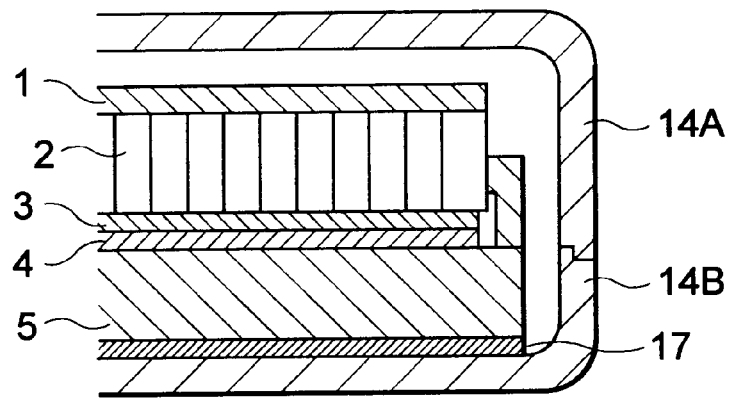
FIGS. 4A to 4C are partial sectional views showing the characteristic features of another embodiment of the present invention.
Figure 4B:
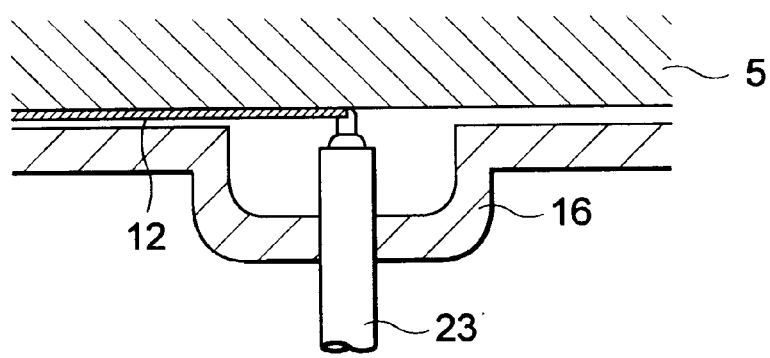
Figure 4C:
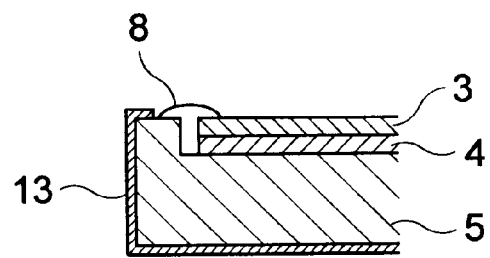

The convex portions 15 of the container 14 need not be formed at positions corresponding to the projecting portions 6 and 9 (FIG. 4A). In this case, the substrate 5 is preferably fixed to the container 14 with an adhesive 17 or the like. The interconnection 12 electrically connecting the electrode extraction terminal 7 and the FPC connector 11 shown in FIGS. 1A and 1B may be formed along the outer periphery of the substrate 5 without extending through the via hole 10 (FIG. 4C). Alternatively, without using the FPC connector 11, the interconnection 12 and the cable 23 may be directly connected through an output electrode terminal formed at substantially the central portion of the surface opposite to the incident surface (FIG. 4B).

In this embodiment, the CCD is used as a solid-state image sensing device. However, another image sensing device such as a BBD (Bucket Brigade Device) or MOS (Metal Oxide Semiconductor) device may be used as the solid-state image sensing device.

As has been described above, according to the present invention, since the projecting portions for adjusting the position of the optical fiber plate to be mounted on the substrate are formed, the optical fiber plate can be accurately set. For this reason, the optical fiber plate can be easily fixed. In addition, the optical fiber plate need not be made large in consideration of the accuracy error in fixing, so the entire apparatus can be made compact.

Furthermore, when a thin plate of copper tungsten is used as the X-ray shielding member, an X-ray shielding member having an accurately flat surface and good affinity to the container can be formed.

The technique of the present invention can be applied to various compact image photographing apparatuses.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

What is claimed is:

1. An X-ray image pickup apparatus for intraoral radiography, which is inserted into an oral cavity and used for radiograph a dentition, comprising:

a phosphor which emits a visible light in response to an incident X-ray;

an optical fiber plate formed by mixing lead into an optical fiber, the plate being formed into a plate shape by bundling a plurality of optical fibers and having said phosphor on an X-ray incident surface formed by end faces of fibers;

a solid-state image sensing device constituted by two-dimensionally pixels array which converts the visible light image into an electrical signal and having said optical fiber plate on a light incident surface facing a surface of opposite to said surface;

an X-ray shielding member arranged on a back plate of said solid-state image sensing device to absorb and shield the X-ray;

a substrate for disposing said solid-state image sensing device via said X-ray shielding member, having an electrode extraction terminal electrically connected to a driving power supply terminal of said solid-state image sensing device and an output terminal of the electrical signal, and, on X-ray incident surface, a plurality of projecting portions projecting to a direction of an X-ray incident around said optical fiber plate from at least three sides so that the side surfaces of said projecting portions are in contact with or close to corresponding side surfaces of said optical fiber plate;

a container for sealing said substrate together with components stacked on said substrate; and a flexible cable having one end electrically connected to said electrode extraction terminal and the other end extracted outside said container and connected to an external driving power supply and an image display unit.

2. An apparatus according to claim 1, wherein each of said projecting portions of said substrate has an overhang portion toward a corresponding side surface of said optical fiber plate so that a distal end of said overhang portion is in contact with or close to said side surface of said optical fiber plate.

3. An apparatus according to claim 1, wherein said container has a projecting portion at a position corresponding to each of said projecting portions on an inner surface on an X-ray incident surface side.

4. An apparatus according to claim 1, wherein said X-ray shielding member is formed from a thin flat copper tungsten member.

5. An apparatus according to claim 1, wherein said container has a projecting portion for accommodating an output electrode terminal electrically connected to said electrode extraction terminal on a surface opposite to an X-ray incident surface so that one end of said cable is connected to said output electrode terminal in said projecting portion.

6. An apparatus according to claim 1, further comprising a thin FPC connector electrically connected to said electrode extraction terminal, and an FPC detachably connected to said FPC connector, and wherein said cable is connected to said FPC.

* * * * *